US011578296B2

(12) United States Patent
Philippe et al.

(10) Patent No.: US 11,578,296 B2
(45) Date of Patent: Feb. 14, 2023

(54) REINFORCED BARBED CLOSURE

(71) Applicant: CORNING INCORPORATED, Corning, NY (US)

(72) Inventors: James M. Philippe, Sanford, ME (US); Aravind Raghavan Rammohan, Big Flats, NY (US); Paul Kevin Seeto, Clinton, MA (US); Neng Wang, Wooster, OH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 16/463,910

(22) PCT Filed: Nov. 29, 2017

(86) PCT No.: PCT/US2017/063655
§ 371 (c)(1),
(2) Date: May 24, 2019

(87) PCT Pub. No.: WO2018/102379
PCT Pub. Date: Jun. 7, 2018

(65) Prior Publication Data
US 2019/0367857 A1     Dec. 5, 2019

Related U.S. Application Data

(60) Provisional application No. 62/428,243, filed on Nov. 30, 2016.

(51) Int. Cl.
*C12M 1/00* (2006.01)
*B65D 41/02* (2006.01)
(Continued)

(52) U.S. Cl.
CPC ............ *C12M 23/38* (2013.01); *B65D 41/023* (2013.01); *B65D 41/04* (2013.01); *B65D 47/06* (2013.01)

(58) Field of Classification Search
CPC ...... C12M 23/38; B65D 41/023; B65D 41/04; B65D 51/16; B65D 47/12; B65D 47/06;
(Continued)

(56) References Cited

U.S. PATENT DOCUMENTS 3,016,173 A * 1/1962 Stull ...................... B65D 47/06
                                                           222/541.2
3,435,976 A   4/1969 Owens
(Continued)

FOREIGN PATENT DOCUMENTS

CA   2339440 A1 * 9/2001  ............ B65D 47/06
CN   1524052 A    8/2004
(Continued)

OTHER PUBLICATIONS

International Search Report and Written Opinion of the International Searching Authority; PCT/US2017/063655; dated Mar. 16, 2018; European Patent Office.
(Continued)

*Primary Examiner* — Rafael A Ortiz
*Assistant Examiner* — Sanjidul Islam
(74) *Attorney, Agent, or Firm* — Michael G. Panian

(57) ABSTRACT

A closure assembly is provided. The closure assembly includes a cap portion, a tubular neck extending from a top surface of the cap portion, and at least one reinforcing member extending between the top surface of the cap portion and an exterior surface of the tubular neck, wherein the cap portion, the tubular neck and the at least one reinforcing member are a unitary integral piece. The closure assembly design provides stability to the tubular neck and the cap portion when a force is applied to either one or both of the tubular neck and the cap portion.

11 Claims, 5 Drawing Sheets

(51) Int. Cl.
*B65D 41/04* (2006.01)
*B65D 47/06* (2006.01)

(58) Field of Classification Search
CPC .... B65D 25/48; B65D 2205/00; B65D 35/38; B65D 25/40; B65D 2543/00398
USPC ............. 220/288, 293, 367.1; 215/329
See application file for complete search history.

(56) References Cited

U.S. PATENT DOCUMENTS

| | | | |
|---|---|---|---|
| 4,128,184 A | | 12/1978 | Northup |
| 4,322,011 A | | 3/1982 | Mumford |
| 4,397,879 A | * | 8/1983 | Wilson ............... A47J 43/28 220/266 |
| 4,408,699 A | * | 10/1983 | Stock ............... B01L 3/0272 222/149 |
| 4,415,096 A | * | 11/1983 | Ohmi ............... B65D 53/04 215/343 |
| 4,423,821 A | | 1/1984 | McIntosh |
| 5,350,080 A | * | 9/1994 | Brown ............... C12M 23/48 220/62.21 |
| 6,659,310 B1 | * | 12/2003 | Wolpert ............... B65D 47/06 222/109 |
| 6,673,598 B1 | | 1/2004 | Akers et al. |
| 8,985,359 B2 | * | 3/2015 | Bear ............... C12M 27/12 215/309 |
| 8,998,875 B2 | | 4/2015 | Lev et al. |
| 2001/0000602 A1 | * | 5/2001 | Luch ............... B65D 41/3404 215/256 |
| 2009/0152281 A1 | * | 6/2009 | Bowes ............... A45D 19/02 220/694 |
| 2012/0248111 A1 | | 10/2012 | Bear et al. |
| 2015/0274378 A1 | * | 10/2015 | Galownia ............... B65D 1/44 215/337 |

FOREIGN PATENT DOCUMENTS

| | | |
|---|---|---|
| CN | 1882478 A | 12/2006 |
| CN | 103221134 A | 7/2013 |
| CN | 103562089 A | 2/2014 |
| CN | 103648922 A | 3/2014 |
| JP | 57-055862 A | 4/1982 |
| JP | 06-067354 U | 9/1994 |
| JP | 10-318066 A | 12/1998 |
| JP | 2006-204263 A | 8/2006 |
| JP | 2009-126527 A | 6/2009 |
| JP | 2012-519069 A | 8/2012 |
| JP | 2013-543738 A | 12/2013 |
| WO | 2005049446 A1 | 6/2005 |
| WO | 2008/021084 A2 | 2/2008 |
| WO | 2012071249 A1 | 5/2012 |
| WO | 2012138637 A1 | 10/2012 |
| WO | 2012154813 A1 | 11/2012 |

OTHER PUBLICATIONS

Langley et al.; "'Inclusive' Design for Containers: Improving Openability"; Packag. Technol. Sci. 2005; 18; pp. 285-293; 2005.
Langley et al.; "Inclusive Design: Making Packaging Easier to Open for All"; 14th IAPRI World Conference on Packaging; Jun. 13-16, 2004, Lidingo, Sweden.
Langley et al; "The 'Inclusive Engineering' Approach: An Optimum Diameter for Ease of Opening"; 22nd IAPRI Symposium on Packaging; May 22-25, 2005, Campinas, Brazil.
Yoxall et al; "Numerical Simulation of Interaction Between a Threaded Glass Container and a Screw Cap"; Glass Technol., 2000, 41 (1), 30-2.
Chinese Patent Application No. 201780074264.3, Office Action dated Jan. 24, 2022, 12 pages of English Translation only, Chinese Patent Office.
Japanese Patent Application No. 2019-528842, Office Action dated Oct. 4, 2021, 12 pages (6 pages of English Translation and 6 pages of Original Document), Japanese Patent Office.

\* cited by examiner

REINFORCED BARBED CLOSURE

CROSS-REFERENCE TO RELATED APPLICATIONS

This is a national stage application under 35 U.S.C. § 371 of International Application No. PCT/US2017/063655, filed Nov. 29, 2017, which claims the benefit of priority of U.S. Provisional Application Ser. No. 62/428,243 filed on Nov. 30, 2016 the contents of which are relied upon and incorporated herein by reference in their entirety as if fully set forth below.

FIELD

The present disclosure generally relates to closure assemblies having barbed tubular necks, and container systems that incorporate such closure assemblies. In particular, the present disclosure relates to reinforced closure assemblies having barbed tubular necks and container systems that incorporate such closure assemblies.

BACKGROUND

Caps and closure assemblies are a necessary feature of cell culture containers which are preferably provided as a closed system. In certain cell culture container, caps and closure assemblies have been provided with a means for fluidly connecting a source of gas, liquid or other material, such as cell growth media, with the interior of the cell culture container. Various tubes or probes may be attached to such means, and such means may be used to deliver controlled volumes of gas, liquid, or other material to the interior of the container while maintaining a closed system. Conventionally, great care is taken to ensure that no leaking occurs at the location where the container is closed by the cap or closure and also that no contaminants enter the interior of the container at the location where the container is closed by the cap or closure.

Despite taking great care to prevent leaking and/or contamination, conventional caps and closures do not always adequately maintain a closed system. For example, in order to close a cell culture container with a cap or closure and prevent such leaking or contamination as described above, a sufficient force must be applied to the cap or closure in order to adequately close and seal a port in the cell culture container. Oftentimes the application of such a force causes the cap or closure to crack, break or otherwise fail. Similarly, for caps or closures having a means for fluidly connecting external sources with the interior of the cell culture container, the application of force to apply the cap or closure to the cell culture container, or other bending forces (applied, for example, when tubes or hoses are attached to such means) causes such means to crack, break or otherwise fail.

What is needed is a cap or closure assembly that is able to withstand forces applied to the cap or closure assembly when the cap or closure is placed on a port in the cell culture container to close and seal the port.

SUMMARY

According to embodiments of the present disclosure, a closure assembly is provided. The closure assembly includes a cap portion, a tubular neck extending from a top surface of the cap portion, and at least one reinforcing member extending between the top surface of the cap portion and an exterior surface of the tubular neck, wherein the cap portion, the tubular neck and the at least one reinforcing member are a unitary integral piece.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Figure 1:
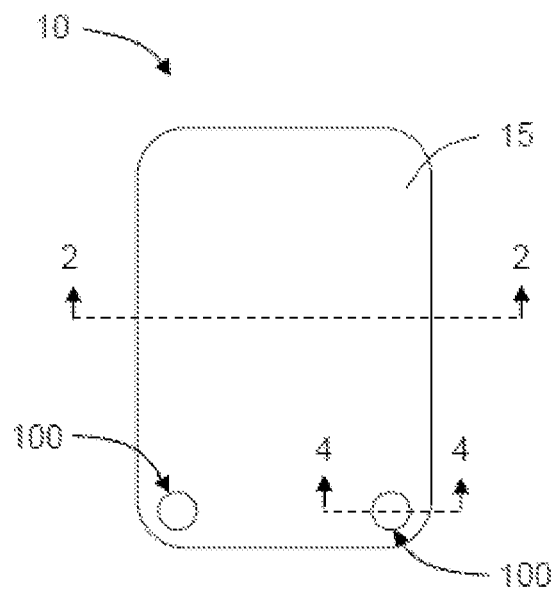
FIG. 1 is a schematic top view of an exemplary cell culture apparatus in accordance with embodiments of the present disclosure.

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

As used herein, "have," "having," "include," "including," "comprise," "comprising" or the like are used in their open ended sense, and generally mean "including, but not limited to."

All scientific and technical terms used herein have meanings commonly used in the art unless otherwise specified. The definitions provided herein are to facilitate understanding of certain terms used frequently herein and are not meant to limit the scope of the present disclosure.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

Embodiments of the present disclosure relate to closure assemblies including a cap portion with a tubular neck extending from a top surface of the cap portion. The tubular neck and the cap portion are preferably molded as a unitary integral piece. The closure assemblies further include at least one reinforcing element integrally formed on the closure assembly and extending between an exterior surface of the tubular neck and the top surface of the cap portion, wherein the at least one reinforcing element provides stability to the tubular neck and the cap portion when a force is applied to either one or both of the tubular neck and the cap portion. Closure assemblies described herein may be used in any suitable cell culture system. For example, jars, flasks, bottles, plates, beakers, tubes, bags, perfusion chambers, bioreactors, Corning Incorporated's CellSTACK® culture chamber devices, and fermenters may be readily adapted to incorporate a closure assembly or components thereof.

Figure 2:
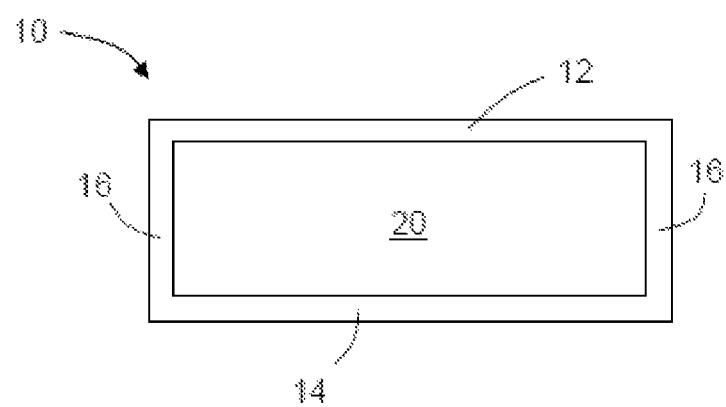
FIG. 2 is a schematic cross sectional view of the apparatus depicted in FIG. 1, taken through line 2-2.

By way of example and referring to FIG. 1, a schematic top view of an example of a cell culture apparatus 10 that incorporates a port 100, as described herein, is shown. The depicted cell culture apparatus 10 has a top surface 15 and two ports 100 extending from the top surface. While two ports are shown, it will be understood that a cell culture apparatus 10 may include any suitable number of ports 100. It will also be understood that while the ports 100 are depicted as extending from a top surface 15 of the apparatus 10, one or more ports 100 may be positioned at any suitable location of the apparatus 15 to provide access to an interior chamber of the apparatus. Referring now to FIG. 2, a schematic cross-sectional view, taken through line 2-2 of an embodiment of a cell culture apparatus of FIG. 1, is shown. The depicted apparatus 10 includes a cell culture chamber 20 defined by top 12, bottom 14, and side 16 walls. The top wall 12 of the culture chamber 20 also serves as the top of the apparatus in the depicted embodiment. One or more port 100 (see, e.g., FIG. 1) is in communication with the chamber 20 to provide access to the chamber. Of course, while the apparatus 10 depicted in FIG. 2 is a fairly simple apparatus, it will be understood that more complex apparatuses, such as those having multiple cell culture chambers, tracheal chambers, or chambers for introducing fluid and/or other components to adjacent cell culture chambers, may be modified to include a port or closure assembly as described herein. In any case, a port described herein provides access to one or more chamber of a cell culture apparatus.

A port as described herein may be made from any suitable material, such as a hard plastic material, glass, metal or the like. Examples of suitable plastic materials include high density polyethylene (HDPE), polypropylene, polycarbonate, polystyrene and the like. Preferably the port is formed from biocompatible material. In some embodiments, the port is formed from the same or similar material as the housing of the cell culture apparatus. The port may be integrally molded with a portion of the housing of the cell culture apparatus, may be welded, adhered, or otherwise affixed to the cell culture apparatus.

A closure assembly as described herein may be made from any suitable material, such as a hard plastic material, metal or the like. Examples of suitable plastic materials include high density polyethylene (HDPE), polypropylene, polycarbonate, and the like. Preferably the closure assembly is formed from biocompatible material. In some embodiments, the closure assembly is formed from the same or similar material as the port. The closure assembly may be formed by any suitable process, such as molding.

As used herein, the term "fluid" is used to denote any substance capable of flowing, such as liquids, liquid suspensions, gases, gaseous suspensions, or the like, without limitation. The term "fluid and/or other components" is used throughout the present disclosure to refer to fluid which may include cell culture media having nutrients for cell growth, cells, byproducts of the cell culture process, and any other biological materials or components that may conventionally be added or formed in a bioprocess system. Structured bags and other vessels described herein may include one or more cells or reagents. Additionally, the bags may include cell culture media. Cell culture media may be for example, but is not limited to, sugars, salts, amino acids, serum (e.g., fetal bovine serum), antibiotics, growth factors, differentiation factors, colorant, or other desired factors. Common culture media that may be provided in the bag includes Dulbecco's Modified Eagle Medium (DMEM), Ham's F12 Nutrient Mixture, Minimum Essential Media (MEM), RPMI Medium, and the like. Any type of cultured cell may be included in the bag including, but not limited to, immortalized cells, primary culture cells, cancer cells, stem cells (e.g., embryonic or induced pluripotent), etc. The cells may be mammalian cells, avian cells, piscine cells, etc. The cells may be of any tissue type including, but not limited to, kidney, fibroblast, breast, skin, brain, ovary, lung, bone, nerve, muscle, cardiac, colorectal, pancreas, immune (e.g., B cell), blood, etc. The cells may be in any cultured form in the bag including disperse (e.g., freshly seeded), confluent, 2-dimensional, 3-dimensional, spheroid, etc. In some embodiments, cells are present without media (e.g., freeze-dried, in preservative, frozen, etc.).

Figure 3:
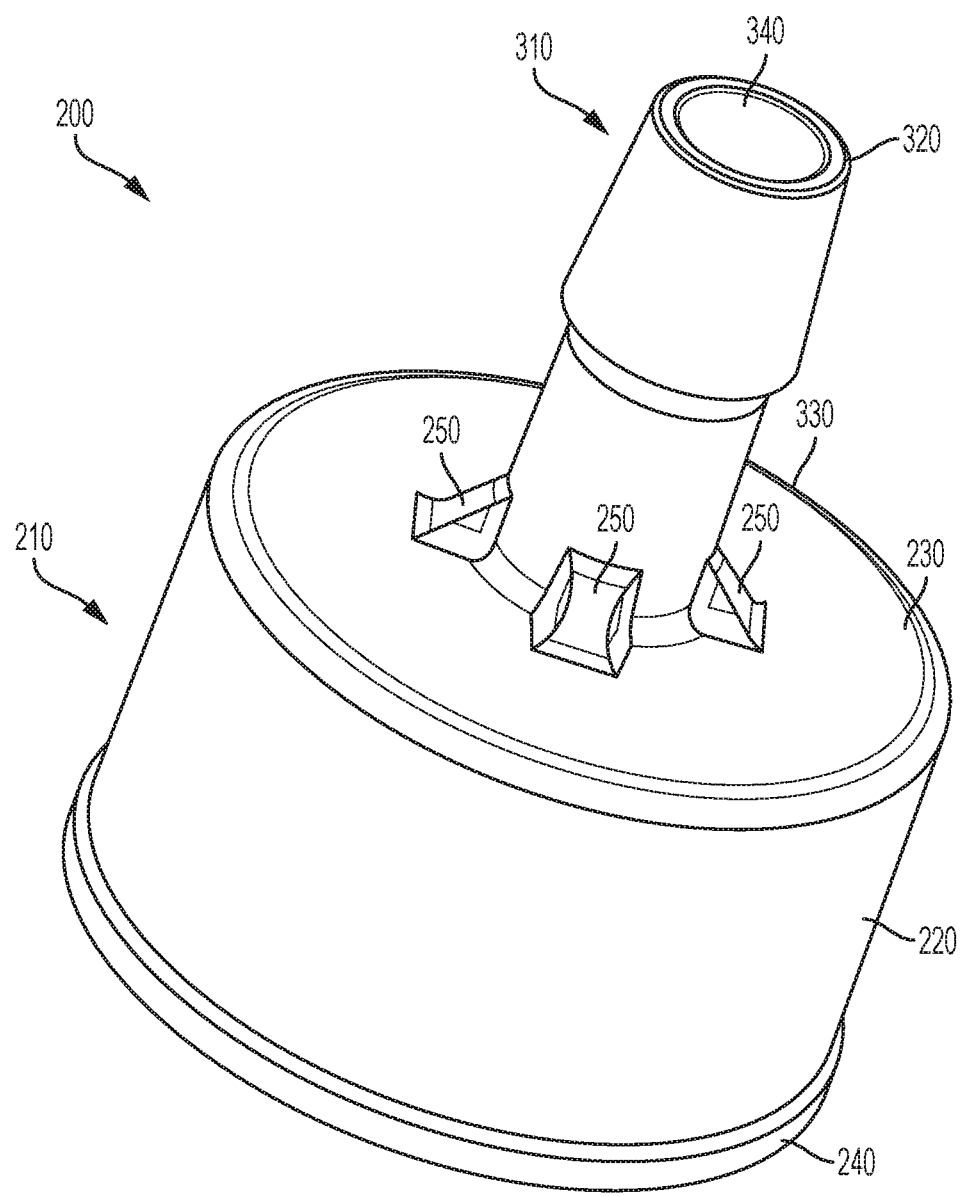
FIG. 3 illustrates a closure assembly in accordance with embodiments of the present disclosure.
Figure 4:
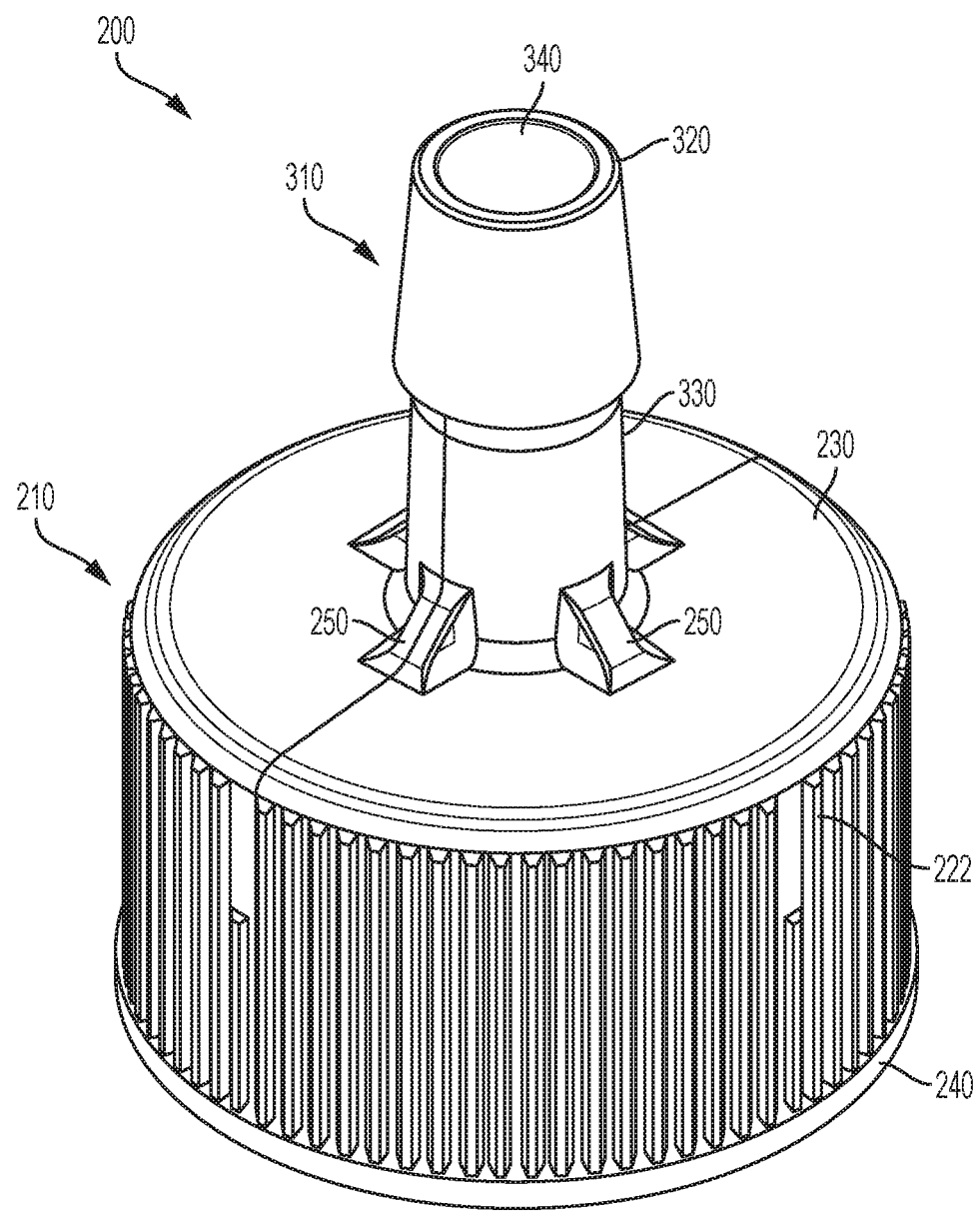
FIG. 4 illustrates a closure assembly in accordance with embodiments of the present disclosure.
Figure 5:
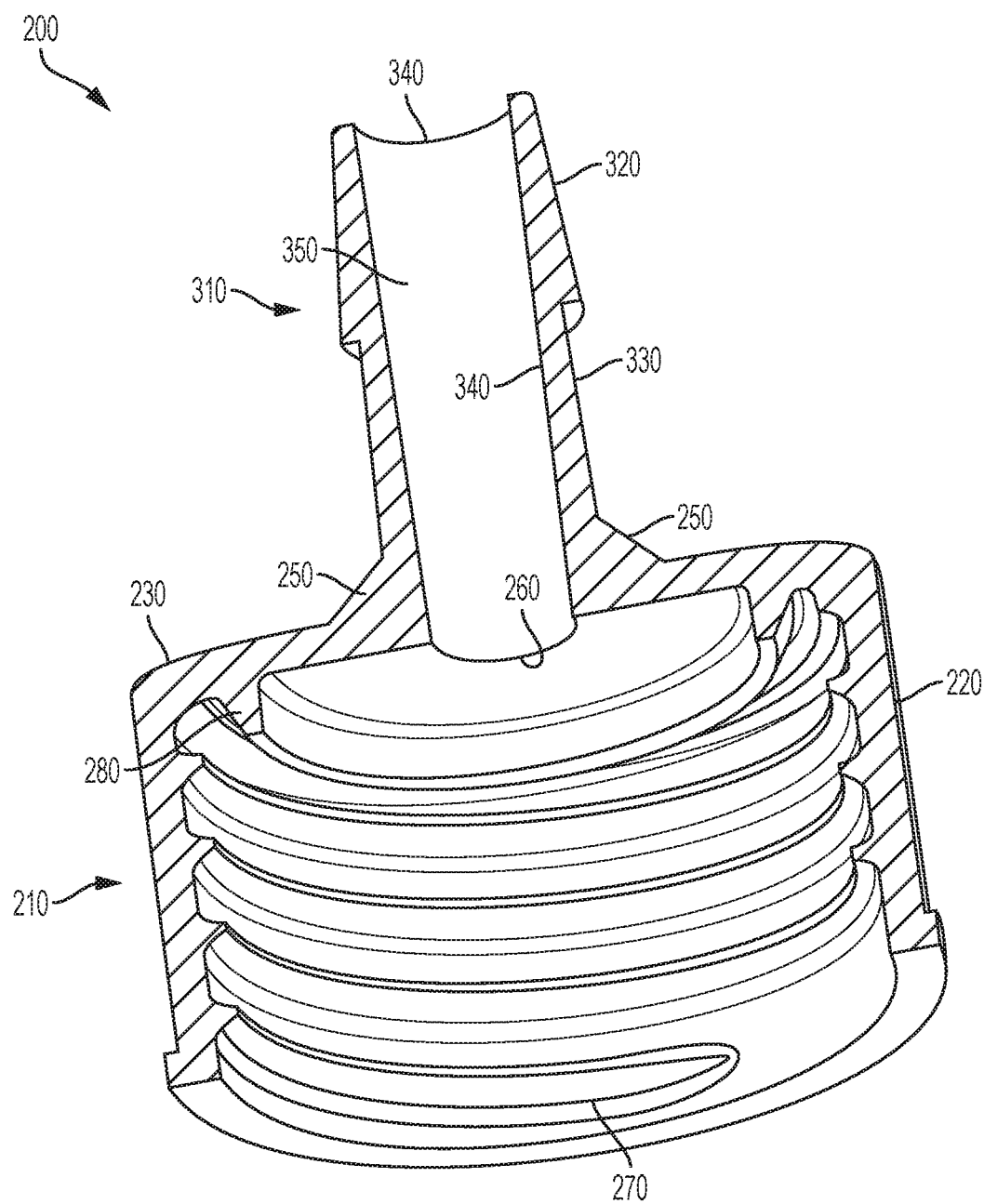
FIG. 5 is a cross sectional view of a closure assembly in accordance with embodiments of the present disclosure.

With reference to FIGS. 3, 4 and 5, closure assemblies 200 in accordance with embodiments of the present disclosure include a cap portion 210 with a tubular neck 310 extending from a top surface 230 of the cap portion 210. The tubular neck 310 includes a neck opening 340 and an interior surface 340 which bounds a passage 350 that longitudinally extends from the neck opening 340 and through the tubular neck 310. The passage 350 is configured to provide fluid communication between the neck opening 340 and a cap portion opening 260, wherein the passage 350 is contiguous with the cap portion opening 260. The passage 350 may be defined concentrically with a longitudinal axis of the tubular neck 310, such that the passage 350 may provide a substantially straight flowpath for fluid and/or other components through the tubular neck 310. The tubular neck 310 further includes an exterior surface 330 which includes barbs 320 or other protrusions extending therefrom.

The cap portion 210 includes an annular sidewall 220 extending from the top surface 230 of the cap portion 210. As shown in FIG. 3, the annular sidewall 220 may include an extension 240 at the bottom of the cap portion 210 which extends beyond the width of the rest of the annular sidewall 220. As shown in FIG. 5, on the interior of the annular sidewall 220, the cap portion 210 further includes internal threads 270 configured to cooperate with external threads of the port so that the closure assembly 200 may be twisted until the cap portion 210 and the port are engaged. The underside of the top surface 230 of the cap portion 210 further includes an annular skirt 280 which extends downward from the top surface 230 of the cap portion 210. The annular skirt 280 is of lesser diameter than, and is concentric with, the annular sidewall 220 and is configured to fit inside a port of a cell culture apparatus. As with conventional twist caps, the cooperation between walls of a cell culture apparatus port and the annular skirt 280 provides a substantially leak-tight seal between the closure assembly 200 and the port of the cell culture apparatus.

FIG. 4 illustrates a closure assembly in accordance with embodiments of the present disclosure that is similar to the closure assembly shown in FIG. 3. The same reference numerals used in FIG. 3 are used in FIG. 4 to refer to the same or like parts. As shown, the closure assembly 300 may include an outer surface of the annular sidewall 220 having at least one knurl 222. The at least one knurl 222, or in the assembly shown in FIG. 4 the plurality of knurls 222, aid in gripping the cap portion 210 of the closure assembly.

Figure 6:
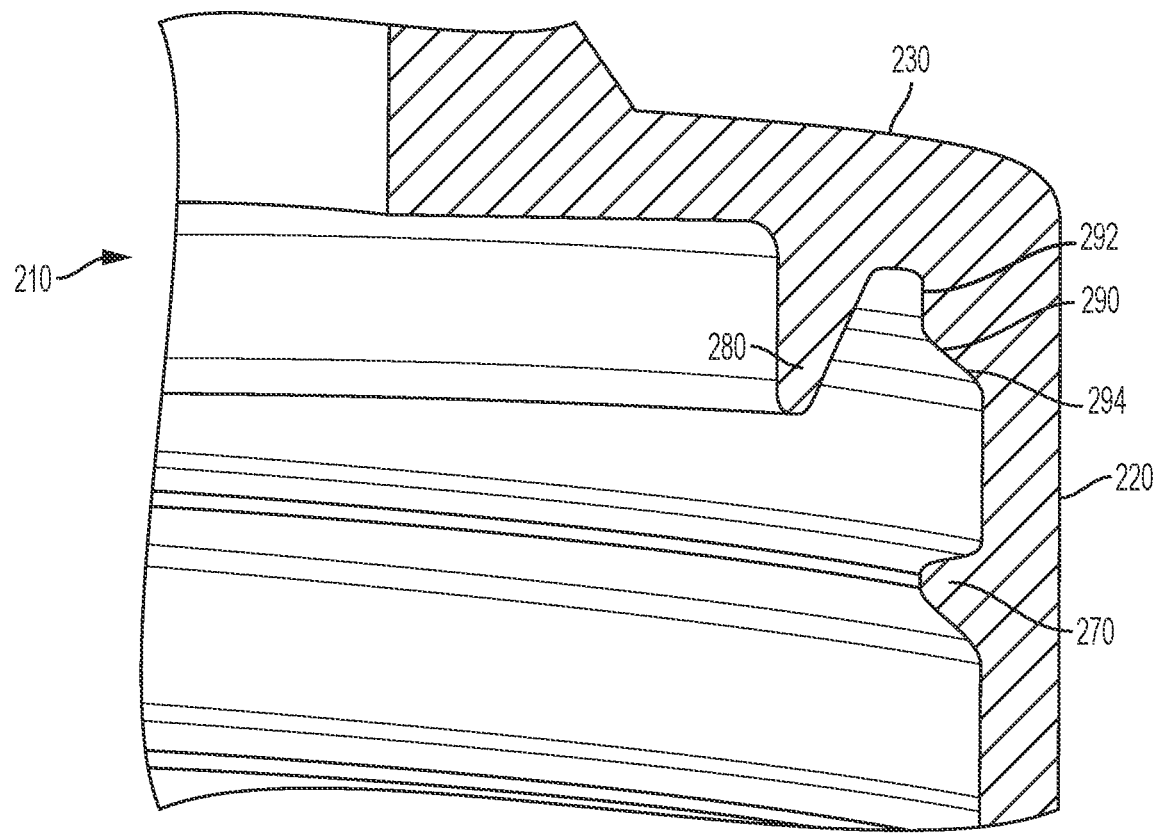
FIG. 6 is a cross sectional view of a portion of a closure assembly in accordance with embodiments of the present disclosure.

As shown in FIGS. 5 and 6, the cap portion 210 further includes a shoulder 290 which extends downward from the top surface 230 of the cap portion 210 such that a first surface 292 of the shoulder 290 is substantially opposite a surface of the annular skirt 280. The shoulder 290 also extends outward from an interior wall of the annular sidewall 220 of the cap portion 210 such that a second surface 294 of the shoulder 290 faces the internal threads 270. Generally, at least one of the first surface 292 and the second surface 294 of the shoulder 290 engages the outside surface of a port of a cell culture apparatus and further promotes effective sealing of the cap portion 210.

According to embodiments of the present disclosure, closure assemblies 200 as described herein include a distance between the annular skirt 280 and the shoulder 290. As used herein, the distance between the annular skirt 280 and the shoulder 290 refers to a straight line measurement of the length between an outer wall of the annular skirt (i.e. a wall portion closest to the annular sidewall 220) and the first surface of the shoulder 290. The distance between the annular skirt 280 and the shoulder 290 may be greater than about 0.010 inches. For example, the distance between the annular skirt 280 and the shoulder 290 may be greater than about 0.015 inches, or greater than about 0.020 inches or greater than about 0.025 inches, or even greater than about 0.030 inches. The distance between the annular skirt 280 and the shoulder 290 may be between about 0.010 inches and about 0.035 inches, or between about 0.015 inches and about 0.030 inches. Inventors have discovered that an increase in the distance between the annular skirt 280 and the shoulder 290 as compared to conventional twist caps provides stability when a force (particularly a twisting force) is applied to the cap portion 210 and that a greater force can be applied to the closure assemblies 200 as described herein without the closure assemblies 200 cracking, breaking or otherwise failing.

Referring again to FIG. 3, closure assemblies 200 in accordance with embodiments of the present disclosure further include at least one reinforcing element 250. The at least one reinforcing element 250 is integrally formed on the closure assembly 200 and extends between the exterior surface 330 of the tubular neck 310 and the top surface 230 of the cap portion 210. The at least one reinforcing element 250 includes an angled portion which spans the distance between the exterior surface 330 of the tubular neck 310 and the top surface 230 of the cap portion 210. The at least one reinforcing element 250 provides areas of increased thickness to both the tubular neck 310 and the cap portion 210, and is configured to provide stability to the tubular neck 310 and the cap portion 210 when a force is applied to either one or both of the tubular neck 310 and the cap portion 210. Although illustrated in FIG. 3 as four tabs equally spaced around the circumference of the tubular neck 310, closure assemblies in accordance with embodiments of the present disclosure may include any number of reinforcing elements 250 and such reinforcing elements 250 may have any dimension. As one example of an alternative, the at least one reinforcing element 250 may be a single tab extending around the entire circumference of the neck.

Engineering models for closure assembly designs as described herein were developed and compared to models for conventional closure assembly designs. Model 1 is designed in accordance with conventional closure assemblies and had a distance between the annular skirt and the shoulder of 0.0075 inches. Model 2 is a closure assembly having a distance between the annular skirt and the shoulder of 0.025 inches. Model 3 is a closure assembly having a distance between the annular skirt and the shoulder of 0.035 inches. The model designs were created and analyzed using structural analysis software (commercially available from ANSYS, Inc., Canonsburg, Pa.). The cap portions of the different model designs were exposed to a simulated screw torque in which a load of 140.6 lbf was applied to the closure assembly models and stress analysis was performed. The maximum von-Mises Stress was determined for each model and the results are shown in Table I.

TABLE I

| Model No. | Distance Between Annular Skirt and Shoulder (inches) | Maximum von-Mises Stress (psi) |
| --- | --- | --- |
| 1 | 0.0075 | 5145 |
| 2 | 0.025 | 3912 |
| 3 | 0.035 | 3617 |

As can be seen from the results of Table I, an increase in the distance between the annular skirt and the shoulder resulted in a decrease in the maximum von-Mises Stress experienced by the closure assembly when exposed to a screw torque. Using the structural analysis software, the yield strength of the material of the models was determined to be about 4100 psi. With reference to the results of Table I, it can be seen that the conventional closure assembly of Model 1 experienced a maximum von-Mises Stress that is above the yield strength of the material, whereas the closure assembly designs of Model 2 and Model 3 experienced a maximum von-Mises Stress that is below the yield strength of the material. As such, it can be expected that the conventional closure assembly of Model 1 would be more likely than the closure assembly designs of Model 2 and Model 3 to break, crack or otherwise fail when the cap portion is exposed to a screw torque while being twisted to engage with a port of a cell culture apparatus.

Additional engineering models for closure assembly designs as described herein were developed and compared to models for conventional closure assembly designs. Model 4 is designed in accordance with conventional closure assemblies and did not have any reinforcing members as described herein. Model 5 is a closure assembly having a tubular neck which includes an exterior surface having a barb with a 0.04 inch radius and includes four reinforcing members equally spaced around the circumference of the tubular neck. Model 6 is a closure assembly having a tubular neck which includes an exterior surface having a barb with a 0.08 inch radius and includes four reinforcing members equally spaced around the circumference of the tubular neck. The barbed tubular neck of the different model designs were exposed to a simulated bending force in which the force was incrementally increased until the maximum von-Mises Stress reached the yield strength of the material. The maximum load for each closure assembly design was determined for each model and the results are shown in Table II.

TABLE II

| Model No. | Maximum Load (lbf) |
|---|---|
| 4 | 8 |
| 5 | 14 |
| 6 | 15 |

As can be seen from the results of Table II, the addition of reinforcing members to the closure assembly designs resulted in an increase in the maximum load to which the closure assemblies may be exposed without breaking, cracking or otherwise failing. With reference to the results of Table II, it can be seen that the reinforcing members of Model 5 and Model 6 increased the maximum load to which the closure assemblies may be exposed by between about 75% and about 88% as compared to the conventional closure assembly of Model 4. As such, it can be expected that the conventional closure assembly of Model 4 would be more likely than the closure assembly designs of Model 5 and Model 6 to break, crack or otherwise fail when the tubular neck is exposed to a bending force.

According to an aspect (1) of the present disclosure, a closure assembly is provided. The closure assembly comprises: a cap portion; a tubular neck extending from a top surface of the cap portion; and at least one reinforcing member extending between the top surface of the cap portion and an exterior surface of the tubular neck, wherein the cap portion, the tubular neck and the at least one reinforcing member are a unitary integral piece.

According to another aspect (2) of the present disclosure, the closure assembly of aspect (1) is provided, wherein the at least one reinforcing member comprises a plurality of reinforcing members equally spaced around the circumference of the tubular neck.

According to another aspect (3) of the present disclosure, the closure assembly of aspect (1) is provided, wherein the at least one reinforcing member comprises one reinforcing member extending around the entire circumference of the neck.

According to another aspect (4) of the present disclosure, the closure assembly of any of aspects (1)-(3) is provided, further comprising a neck opening, a cap portion opening, and a passage extending within the tubular neck between the neck opening and the cap portion, wherein the passage is contiguous with the cap portion opening.

According to another aspect (5) of the present disclosure, the closure assembly of any of aspects (1)-(4) is provided, wherein the tubular neck further comprises barbs extending from the external surface of the tubular neck.

According to another aspect (6) of the present disclosure, the closure assembly of any of aspects (1)-(5) is provided, wherein the cap portion comprises an annular sidewall extending from the top surface of the cap portion.

According to another aspect (7) of the present disclosure, the closure assembly of aspect (6) is provided, wherein the annular sidewall comprises internal threads extending from an interior wall of the annular sidewall.

According to another aspect (8) of the present disclosure, the closure assembly of any of aspects (1)-(7) is provided, wherein the cap portion comprises an annular skirt extending downward from the top surface of the cap portion, wherein the annular skirt is concentric with the annular sidewall, and wherein the annular skirt comprises a smaller diameter than the diameter of the annual sidewall.

According to another aspect (9) of the present disclosure, the closure assembly of any of aspects (6)-(8) is provided comprising a shoulder having a first surface extending downward from the top surface of the cap portion and a second surface extending outward from an interior wall of the annular sidewall.

According to another aspect (10) of the present disclosure, the closure assembly of aspect (9) is provided comprising a distance between the annular skirt and the first surface of the shoulder, wherein the distance between the annular skirt and the first surface of the shoulder is greater than about 0.010 inches.

According to another aspect (11) of the present disclosure, the closure assembly of aspect (10) is provided, wherein the distance between the annular skirt and the first surface of the shoulder is greater than about 0.015 inches.

According to another aspect (12) of the present disclosure, the closure assembly of any of aspects (10)-(11) is provided, wherein the distance between the annular skirt and the first surface of the shoulder is greater than about 0.020 inches.

According to another aspect (13) of the present disclosure, the closure assembly of any of aspects (10)-(12) is provided, wherein the distance between the annular skirt and the first surface of the shoulder is greater than about 0.025 inches.

According to another aspect (14) of the present disclosure, the closure assembly of any of aspects (10)-(13) is provided, wherein the distance between the annular skirt and the first surface of the shoulder is greater than about 0.030 inches.

According to another aspect (15) of the present disclosure, the closure assembly of aspect (10) is provided, wherein the distance between the annular skirt and the first surface of the shoulder is between about 0.010 inches and about 0.035 inches.

According to another aspect (16) of the present disclosure, the closure assembly of aspect (10) is provided, wherein the distance between the annular skirt and the first surface of the shoulder is between about 0.015 inches and about 0.030 inches.

According to another aspect (17) of the present disclosure, the closure assembly of any of aspects (6)-(16) is provided further comprising at least one knurl on the outer surface of the annular sidewall.

While the present disclosure includes a limited number of embodiments, those skilled in the art, having benefit of this disclosure, will appreciate that other embodiments can be devised which do not depart from the scope of the present disclosure.

What is claimed is:

1. A closure assembly for cell culture containers comprising:
    a cap portion comprising an annular sidewall extending from a top surface of the cap portion and an annular skirt extending downward from the top surface of the cap portion;
    a shoulder having a first surface extending downward from the top surface of the cap portion and a second surface extending outward from an interior wall of the annular sidewall;
    a tubular neck extending from the top surface of the cap portion; and
    a plurality of reinforcing members extending between the top surface of the cap portion and an exterior surface of the tubular neck, wherein each reinforcing member of the plurality of reinforcing members is angled between the top surface of the cap portion and the exterior surface of the tubular neck, wherein, for the closure assembly comprising the plurality of reinforcing members, the maximum load to which the closure assembly may be exposed to before breaking or cracking when the tubular neck is exposed to a bending force is increased by between 75% and 88% compared to a conventional closure assembly having no reinforcing members, wherein the cap portion, the tubular neck and the plurality of reinforcing members are a unitary integral piece, wherein the annular skirt is concentric with the annular sidewall and comprises a smaller diameter than the diameter of the annular sidewall, and wherein the distance between the annular skirt and the first surface of the shoulder is between about 0.015 inches and about 0.035 inches.

2. The closure assembly for cell culture containers of claim 1, wherein the plurality of reinforcing members are equally spaced around the circumference of the tubular neck.

3. The closure assembly for cell culture containers of claim 1, further comprising a neck opening, a cap portion opening, and a passage extending within the tubular neck between the neck opening and the cap portion, wherein the passage is contiguous with the cap portion opening.

4. The closure assembly for cell culture containers of claim 1, wherein the tubular neck further comprises at least one barb extending from the external surface of the tubular neck.

5. The closure assembly for cell culture containers of claim 1, wherein the annular sidewall comprises internal threads extending from an interior wall of the annular sidewall.

6. The closure assembly for cell culture containers of claim 1, wherein the distance between the annular skirt and the first surface of the shoulder is between about 0.020 inches and about 0.035 inches.

7. The closure assembly for cell culture containers of claim 1, wherein the distance between the annular skirt and the first surface of the shoulder is between about 0.025 inches and about 0.035 inches.

8. The closure assembly for cell culture containers of claim 1, wherein the distance between the annular skirt and the first surface of the shoulder is between about 0.030 inches and about 0.035 inches.

9. The closure assembly for cell culture containers of claim 1, wherein the distance between the annular skirt and the first surface of the shoulder is between about 0.020 inches and about 0.030 inches.

10. The closure assembly for cell culture containers of claim 1, further comprising at least one knurl on the outer surface of the annular sidewall.

11. The closure assembly for cell culture containers of claim 1, wherein the cap portion is configured to threadably connect to a port of a cell culture vessel.

* * * * *